United States Patent [19]

Mitra et al.

[11] Patent Number: 4,831,109

[45] Date of Patent: May 16, 1989

[54] COPOLYMERIZABLE UV STABILIZERS

[75] Inventors: Sumita B. Mitra; Smarajit Mitra, both of Woodbury, Minn.

[73] Assignee: Minnesota Mining and Manufacturing Company, St. Paul, Minn.

[21] Appl. No.: 57,354

[22] Filed: Jun. 2, 1987

Related U.S. Application Data

[62] Division of Ser. No. 771,307, Aug. 30, 1985, Pat. No. 4,691,059.

[51] Int. Cl.$^4$ .................. C08G 8/02; C08G 14/00
[52] U.S. Cl. ..................... 528/125; 528/73; 528/74
[58] Field of Search ............... 528/125, 73, 74

[56] References Cited

U.S. PATENT DOCUMENTS

| | | | |
|---|---|---|---|
| 3,086,988 | 4/1963 | Gordon | 568/333 |
| 3,128,312 | 4/1964 | Edgerton | 260/591 |
| 3,359,306 | 12/1967 | Farnham et al. | 260/521 |
| 3,366,668 | 1/1968 | Strobel et al. | 260/475 |
| 3,385,910 | 5/1968 | Tocker | 260/860 |
| 3,391,110 | 7/1968 | Coleman | 260/47 |
| 3,518,175 | 6/1970 | Bell | 522/46 |
| 3,981,887 | 9/1976 | Gante et al. | 260/327 |
| 4,076,727 | 2/1978 | Zey et al. | 260/340.7 |
| 4,111,771 | 9/1978 | Darms et al. | 240/159.22 |
| 4,189,409 | 2/1980 | Minagawa et al. | 260/23 |
| 4,199,420 | 4/1980 | Photis | 204/159.15 |
| 4,284,756 | 8/1981 | Horner | 528/128 |
| 4,318,791 | 3/1982 | Felder et al. | 204/159.23 |
| 4,354,016 | 10/1982 | Rashbrook et al. | 528/128 |
| 4,374,984 | 2/1983 | Eichler et al. | 544/80 |
| 4,456,746 | 6/1984 | Horner | 528/128 |
| 4,585,876 | 4/1986 | Fischer et al. | 548/423 |

FOREIGN PATENT DOCUMENTS

| | | |
|---|---|---|
| 0002408 | 6/1979 | European Pat. Off. |
| 2121525 | 11/1972 | Fed. Rep. of Germany |
| 2316291 | 10/1974 | Fed. Rep. of Germany |

OTHER PUBLICATIONS

Chemical Abstracts, vol. 83, 1975, p. 50, Abstract No. 165233e, Columbus Ohio, VS; & CZ-A-156 703 (Z Manasek et al.) 15-02-1974.

*Primary Examiner*—John Kight
*Assistant Examiner*—M. L. Moore
*Attorney, Agent, or Firm*—Donald M. Sell; Walter N. Kirn; Lorraine R. Sherman

[57] ABSTRACT

This invention describes UV-stabilized step growth polymers such as polyesters, polyurethanes, polycarbonates, and combination thereof. The UV-stabilizing moieties present in these polymers comprise chemically bound, pendant ortho-hydroxydiphenyl ketone based moieties. The polymers are especially useful as protective films and fibers which are highly resistant to ultraviolet (UV) and sunlight degradation.

17 Claims, No Drawings

COPOLYMERIZABLE UV STABILIZERS

This is a division of application Ser. No. 771,307, filed Aug. 30, 1985, now U.S. Pat. No. 4,691,059.

FIELD OF THE INVENTION

This invention relates to step growth polymerizable ultraviolet (UV) stabilizers and polymers produced therefrom. In another aspect, a process for condensing monomeric UV stabilizers with multifunctional monomers is disclosed. The polymers are useful as protective films and fibers which are resistant to ultraviolet and sunlight degradation.

BACKGROUND OF THE INVENTION

Many organic polymeric materials on and after exposure to light, especially ultraviolet (UV) light, degrade as shown by yellowing, embrittlement, and eventual breakdown of the polymeric materials. Common step growth polymers such as polyesters and polyurethanes are vulnerable, especially to UV light, and it has long been a practice to blend small amounts of UV stabilizers into thermoplastic polymers to arrest or inhibit such degradation.

Among the classes of UV stabilizers used are 2-hydroxybenzophenones and their derivatives, which, when blended with polymers, have been partially effective in their ability to arrest UV degradation. Unfortunately, significant amounts of these stabilizers can be lost from the polymers due to blooming, exudation, volatilization, solvent extraction during fabrication and cleaning, and in other end uses. The problem is most severe in articles which have a high surface area to volume ratio, such as fibers and films.

Direct introduction of the 2-hydroxybenzophenone moiety into polymers to prevent or arrest UV degradation has been taught. U.S. Pat. No. 3,391,110 describes copolymerizable 2-hydroxybenzophenones; however, they possess only one polymerizable group and thus can serve only to terminate a polymer or growing polymer chain. This limits both the molecular weight of the polymer and its useful mechanical properties.

U.S. Pat. Nos. 3,366,668, 3,385,910, 4,189,409, 4,354,016, and 4,456,746, describe polymers containing the 2-hydroxybenzophenone moiety and U.S. Pat. No. 4,284,756 describes a polymer containing the 1-hydroxy-xanth-9-one moiety wherein these moieties are part of the backbone of the polymer chain.

SUMMARY OF THE INVENTION

The present invention provides step growth-polymerizable UV stabilizing monomers containing UV stabilizing ortho-hydroxydiphenyl ketone based moieties. In another aspect, the UV stabilizing monomers of the invention can be bulk polymerized with multifunctional monomers to produce polymers having pendant UV stabilizing ortho-hydroxydiphenyl ketone moieties.

The background art has taught the incorporation, of one or more ortho-hydroxydiphenyl ketone moieties into the backbone of condensation polymers. In contrast, the present invention teaches UV-stabilized step growth polymers such as polyesters, polycarbonates, polyurethanes and the like wherein ortho-hydroxy substituted diphenyl ketone moieties are pendantly incorporated into the condensation polymers. Thus, in polymers of this invention, the polymer repeating unit is not interrupted in its backbone portion by UV-stabilizing groups. Rather, the UV-stabilizing groups are pendant to the main chain. In the present invention, random polymers are provided which have chemically bound, UV-stabilizing groups pendant to the polymer backbone.

In this application:

"backbone" means main chain of a polymer, exclusive of pendant or end groups;

"pendant" means suspended from the main chain of a polymer and not an end group;

"polyester" means a polymer having structural units linked by ester groupings; obtained by condensation of polycarboxylic acids with polyhydric alcohols;

"polyurethane" means a group of synthetic materials characterized by a plurality of urethane groups —NH-COO—;

"polycarbonate" means a polyester of carbonic acid, made by the polymeric condensation of carbonic acid or its derivatives with a polyhydric alcohol;

"alk", "alkyl" or "alkoxyalkyl" means a group having 1 to 20 carbon atoms in the "alk" or "alkyl" portion and up to 3 non-connected oxygen atoms in the "alkoxy" portion;

"ar" or "aryl" means phenyl, biphenyl, or polynuclear aromatic hydrocarbon groups of 6 to 20 carbon atoms;

"step growth polymerization" means a multistep reaction for the formation of polymers by chemical reactions such as condensation, addition, and elimination of small molecules; and "ortho-hydroxydiphenyl ketone based moiety" or "2-4-dihydroxybenzophenone based compound" means a moiety or compound containing a benzophenone structure which can include bridging group W as defined below.

DETAILED DESCRIPTION

The polymerizable UV stabilzing hydroxy monomers of this invention can be represented by formula I:

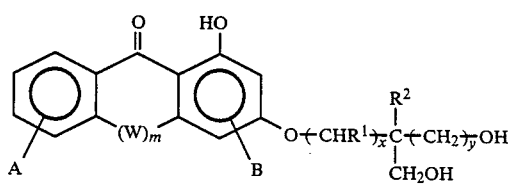

where $R^1$ and $R^2$ can be the same or different and each is selected from hydrogen and substituted or unsubstituted alkyl, alkoxyalkyl, aryl, aryloxyalkyl, alkoxyaryl, aralkyl or alkaryl groups, or $R^1$ and $R^2$ together can form an aliphatic cyclic structure of 5 to 7 atoms which can include carbon and zero to two non-connected oxygen atoms, wherein $R^1$ and $R^2$ together can total from zero to forty carbon atoms; $R^1$ and $R^2$ can be substituted by a non proton-donating group (non-nucleophilic group) which preferably is halogen (Cl, F, Br), $NO_2$, CN, an aldehyde group, an acyl group having 1 to 10 carbon atoms, or an aroyl group having 6 to 10 carbon atoms;

x can be an integer from 0 to 20;

y can be 0 or 1; provided that at least one of x and y is not 0;

m can be 0 or 1;

A and B may be the same or different and can represent a total of zero to eight monovalent substituents on the aromatic rings selected from the class consisting of (1) hydrogen, halogen, or nitrogen-containing groups selected from nitro, tertiary amine, amido, cyano, and (2) substituted or unsubstituted alkyl, aryl, alkenyl, aralkyl, alkaryl, alkoxy, aryloxy, aralkyloxy, alkaryloxy, aryloxyalkyl, and thioalkyl, these groups having 1 to 20 carbon atoms and up to 6 non-connected oxygen and sulfur atoms, which groups can be substituted by halogen or a nitrogen-containing group such as nitro, tertiary amino, cyano, or amido, or A and B can be linked to the aromatic rings by divalent groups such as keto, sulfoxide, sulfone groups and the like, with the proviso that when m is 0, W is not present, then a benzophenone structure is present and the valency is satisfied by hydrogen atoms, and when m=1, then W is a single bond or a divalent group

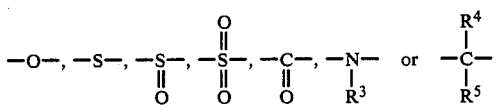

in which $R^3$ can be a substituted or unsubstituted alkyl, alkoxyalkyl, aryl, aryloxyalkyl, alkoxyaryl, aralkyl, or alkaryl group, which can be substituted by a non proton-donating group which preferably is halogen (Cl, F, Br), $NO_2$, CN, an aldehyde group, an acyl group having 1 to 10 carbon atoms, or an aroyl group having 6 to 10 carbon atoms;

$R^4$ and $R^5$ independently can be the same as $R^1$ and $R^2$ which are defined above; when W is a single bond a fluorenone structure is present.

The general structure of the condensation polymers prepared in this invention are represented by formula II:

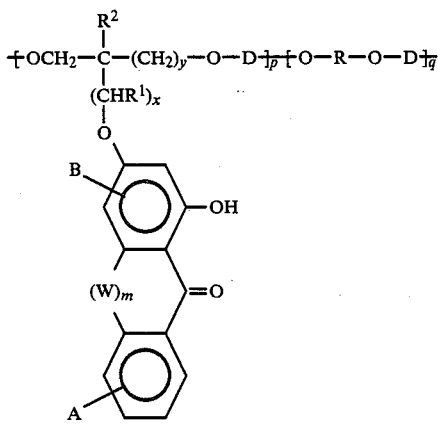

wherein $R^1$, $R^{22}$, x, y, m, A, and B are as defined above, and R can be any divalent organic group having 1 to 20 carbon atoms; preferably R is a linear or cyclic aliphatic or aromatic group, or combinations thereof, containing up to 3 non-connected N, S, and O hetero atoms; more preferably R contains 1 to 10 carbon atoms and is an alkylene or arylene group, or an alkylene group interrupted by phenylene; D can be

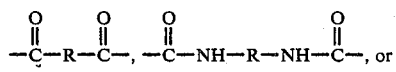

$$-\overset{O}{\underset{\|}{C}}-O-R-O-\overset{O}{\underset{\|}{C}}-,$$

wherein R is as defined above.

Representative multifunctional monomers containing acid, acid anhydride, acid chloride, ester, and/or isocyanate functionality can undergo condensation polymerization with stabilizer hydroxy compound I and optionally with mixtures of compound I and other polyhydroxy compounds to provide polymer II which can be a polyester, polycarbonate, polyurethane, or combinations thereof; the polymer units repeating p times are comprised of the UV stabilizing moieties, and the units repeating q times resulting from the multifunctional condensation polymerizable monomers, where p can b equal to or greater than one and q can be zero or greater than zero; when q is not zero, then the ratio of q to p can be in the range of 1:10,000 to 10,000:1, preferably the ratio of q to p is in the range 10:1 to 10,000:1. When q is equal to zero, a homopolymer of pendant UV stabilizing moieties results. The polymeric number average molecular weight of polymer II is in the range of 1,000 to 10,000,000, preferably 10,000 to 1,000,000.

The ratio of the two repeating units p and q may be varied during polymer syntheses to incorporate different amounts of stabilizing moieties into the polymer. Preferably, 0.05 to 5.0% by weight of the stabilizing moiety containing monomer is incorporated. The remainder of the polymer consists of linear, thermoplastic, step growth polymers such as polyester, polyurethane, polycarbonate, etc. and combinations thereof.

As noted above, groups R and D can vary widely. For example,
(a) a UV stabilized polyester of this invention can be provided by reaction of
   (1) 50 mole percent of an aliphatic or aromatic dicarboxylic acid having 2 to 22 carbon atoms and can contain up to 3 non-connected S, N, and O heteroatoms,
   (2) 0 to 49.995 mole percent, preferably 40 to 49.995 mole percent, of a low molecular weight glycol having 2 to 20 carbon atoms such as ethylene glycol, 1,4-butanediol, 1,6-hexanediol, 1,4-dimethylolcyclohexane, or other dimethylol molecules containing aliphatic, aromatic, cycloaliphatic or heterocyclic residues, and
   (3) 0.005 to 50 mole percent, preferably 0.005 to 10 mole percent of a hydroxy compound of formula I;
(b) a UV stabilized polyurethane of this invention can be provided by reaction of
   (1) 50 mole percent of an aliphatic or aromatic diisocyanate having 3 to 22 carbon atoms and can contain up to 3 non-connected N, S, and O hetero atoms,
   (2) 0 to 49.995 mole percents, perferably 40 to 49.995 mole percent, of a low molecular weight glycol having 2 to 20 carbon atoms such as ethylene glycol, 1,4-butanediol, 1,6-hexanediol, 1,4-dimethylolcyclohexane or other dimethylol molecules containing aliphatic, aromatic, cycloaliphatic or heterocyclic residues, and
   (3) 0.005 to 50 mole percent, preferably 0.005 to 10 mole percent, of a hydroxy compound of formula I;
(c) a UV stablized polycarbonate of this invention may be provided by reaction of (1) phosgene or an aliphatic or aromatic bis-chloroformate having 3 to 22 carbon atoms (2) 0 to 49.995 mole percent, preferably 40 to 49.995 mole percent, of a low molecular weight glycol having 2 to 20 carbon atoms such as ethylene glycol, 1,4-butanediol, 1,6-hexanediol, 1,4-dimethylolcyclohexane or other dimethylol molecules containing aliphatic, aromatic, cycloaliphatic or heterocyclic residues or a low molecular weight diphenol such as resorcinol, catechol, hydroquinone, bisphenol A, 4,4'-dihydroxybiphenyl, 4,4'-diphydroxydipenylmethane etc., and (3) 0.005 to 50 mole percent, preferably 0.005 to 10 mole percent, of a hydroxy compound of formula I.

The polymerizable UV stabilizers of this invention can be prepared by the following general reaction for the benzophenone-containing sequence which is shown in the following Flow Chart.

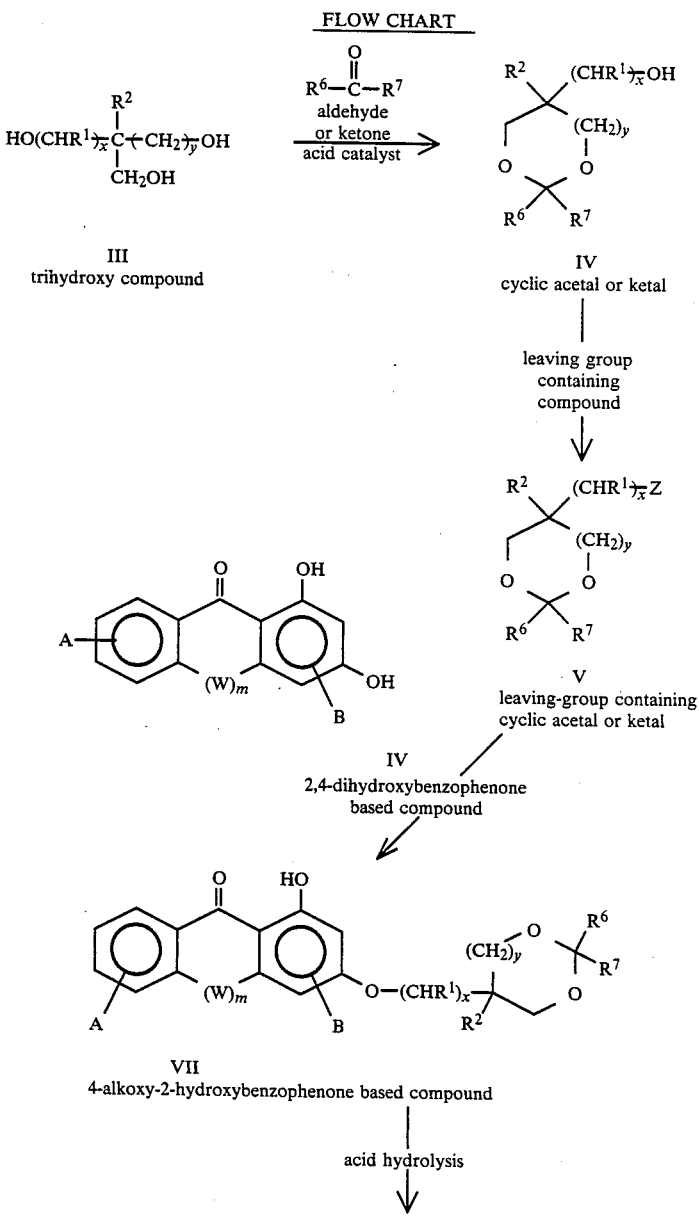

FLOW CHART

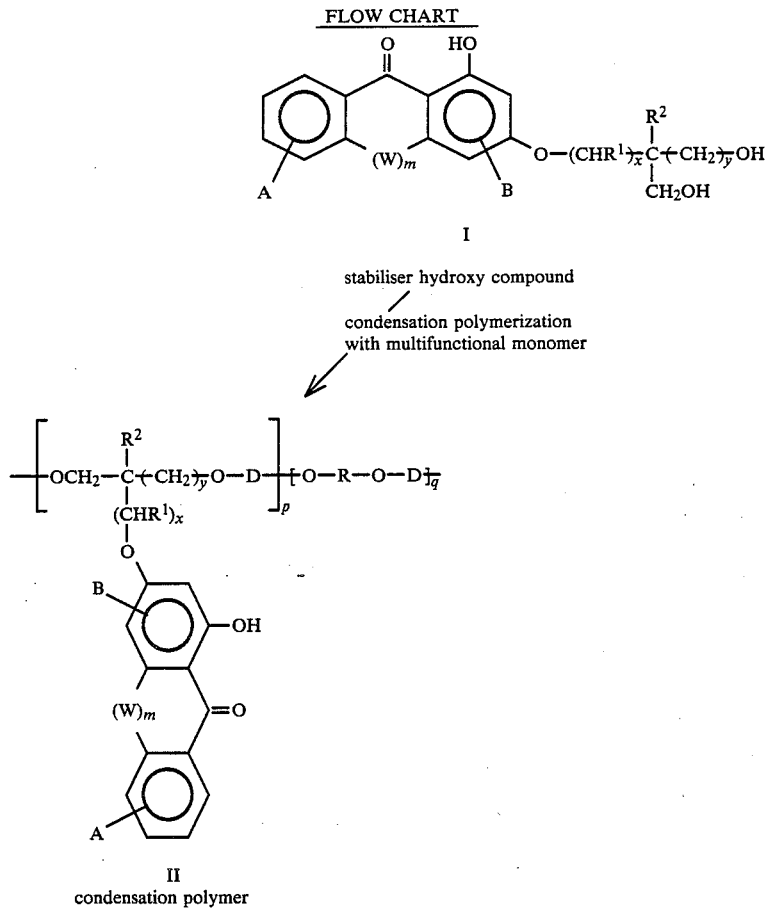

I stabiliser hydroxy compound condensation polymerization
with multifunctional monomer II
condensation polymer A trihydroxy compound of the general formula III

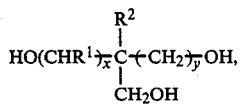    III where $R^1$, $R^2$, x, and y are as previously defined, is reacted with an aldehyde or ketone

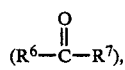

in which $R^6$ and $R^7$ can be independently H, alkyl, aryl, alkoxyalkyl, aryloxyalkyl, aralkyl, or alkaryl, or $R^6$ and $R^7$ together can form an aliphatic cyclic structure having 5 to 7 carbon atoms and up to 2 non-connected oxygen atoms, wherein together $R^6$ and $R^7$ can total from zero to 40 carbon atoms, in the presence of an acid catalyst to convert the aldehyde or ketone to the cyclic acetal or ketal of the formula IV

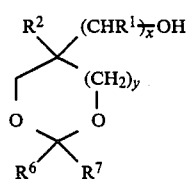    IV where $R^1$, $R^2$, $R^6$, $R^7$, x and y are as defined above. A variety of trihydroxy compounds may be used for the purpose, e.g., glycerol; 2-methylglycerol; 1,2,3-butanetriol; 1,2,4-butanetriol; 1,2,5-pentanetriol; 1,2,6-hexanetriol; 2-methyl-1,2,3-butanetriol; 2-hydroxymethyl-1,3-propanediol; 2-hydroxymethyl-1,3-butanediol; 2-hydroxymethyl-1,4-butanediol; 2-hydroxymethyl-1,5-pentanediol; 2,2-bis(hydroxymethyl)-3-methylhexanol, 2,2-bis(hydroxymethyl)-3-ethylpentanol; 2-hydroxymethyl-2,-methyl-1,3-propanediol; 2-hydroxymethyl-2-methyl-1,3-butanediol; 1-phenylglycerol; 2-phenylglycerol; 2-hydroxymethyl-1-phenyl-1,3-propanediol and 2-hydroxymethyl-2-phenyl-1,3-propanediol.

The aldehyde

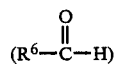

needed for preparing the cyclic acetal may be chosen from a wide variety of materials, the more common ones being formaldehyde, acetaldehyde, propionaldehyde, isobutyraldehyde, chloral, benzaldehyde, o-, m-, and p-nitrobenzaldehyde, m-chlorobenzaldehyde, anisaldehyde, furfural, etc.

To prepare the cyclic ketal, the carbonyl component is a ketone

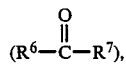

some of the common ones being acetone, methyl ethyl ketone, methyl isobutylketone, cyclopentanone, cyclohexanone, 3-methylcyclohexanone, acetophenone, benzophenone, and the like. Acetone is the preferred ketone for the practice of this invention.

The method of synthesis of the cyclic acetal or ketal from a 1,2- or 1,3-diol and an aldehyde or ketone by acid catalysis is well known in the art. The cyclization is usually brought about by treating the hydroxy compound with an aldehyde or ketone in the presence of an acid catalyst such as hydrogen chloride (or hydrochloric acid), sulfuric acid, perchloric acid, p-toluenesulfonic acid or zinc chloride. The reaction may be carried out in the absence of a solvent, but in this case an inert diluent such as dimethylformamide (DMF), dioxane, ether, benzene or petroleum ether is preferred. By appropriate choice of this diluent, the water formed in the reaction can be removed by distillation. When the reaction reaches completion, the mixture may be neutralized with a weak base such as sodium acetate and dried with a conventional drying agent such as anhydrous sodium sulfate, before isolating the cyclic acetal or ketal by methods well known in the art.

The free alcoholic group of the cyclic acetal or ketal is then converted to one of many functional groups generally known in organic chemistry as a good "leaving" group. By good "leaving" group is meant a functional group (Z) which is easily displaced by another nucleophilic group. Representative examples of these functional groups are the halides (chlorides, bromides or iodides) and the sulfonic acid esters, e.g., p-toluenesulfonates(tosylate), methanesulfonates (mesylate), trifluoromethanesulfonate (triflate) etc., the latter two being the preferred functional good "leaving" groups for this work.

The methanesulfonate ester of the free hydroxyl group is typically prepared by reacting a solution of the alcohol in a non-acidic organic solvent, e.g., methylene chloride, containing a suitable organic base, e.g., triethylamine, with the appropriate amount of methanesulfonyl chloride usually at room temperature or below. When the reaction is complete, the methane sulfonate ester V,

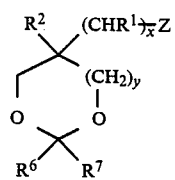

where Z is a $CH_3SO_3-$ group and $R^1$, $R^2$, $R^6$, $R^7$, x and y are as defined above, is typically isolated by distillation under reduced pressure after the usual extractive work up processes to remove acidic or basic impurities.

Chemical conversion of this resultant leaving group-containing cyclic acetal or ketal to the 2-4-dihydroxybenzophenone based compound (which contains the UV stabilizer moiety) is now possible by nucleophilic displacement of the leaving group Z (under conditions known in the art) by the phenolate ion generated from the above benzophenone by deprotonation as will be described below. The 2,4-dihydroxybenzophenone based compounds that may be attached by this technique can be exemplified by the Formula VI

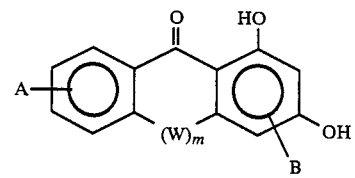

where A, B, W and m are defined above.

Treatment of the 2,4-dihydroxybenzophenone derivative with one equivalent of a suitable base followed by reaction with compounds of Formula V leads predominantly to the formation of the 4-alkoxy-2-hydroxybenzophenone based derivative of the Formula VII

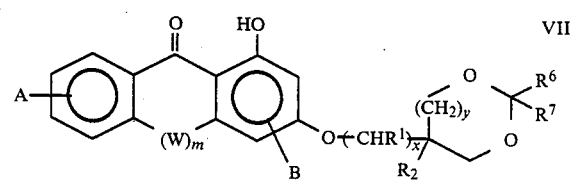

where $R^1$, $R^2$, $R^6$, $R^7$, x, y, A, B, W and m are defined above.

Many suitable organic and inorganic bases may be used for the generation of the phenolate ion, i.e., deprotonation of the 4-hydroxy group of (VI), such as alkali metals or alkaline earth metal hydroxides, alkoxides, or hydrides, the preferred one being sodium hydride in this case, which results in formation of easily removed volatile hydrogen gas as a by-product. Any of the large number of non-acidic organic solvents, such as N,N-dimethylformamide, N,N-dimethylsulfoxide, alcohols, and inert aromatics such as toluene, as known to one skilled in the art, may be used for the nucleophilic displacement reaction to prepare compound VII. The preferred solvent for this step is N,N-dimethylformamide, into which the benzophenone (VI) is dissolved and the sodium hydride is added to generate the phenolate anion. Addition of the sulfonate ester (V) to this mixture results in the formation of compound (VII) through nucleophilic displacement, at about 50° C. to 100° C. for 1-16 hours. The resultant ethers (VII) for the most part are solid materials which can be isolated by the usual filtration techniques.

The cyclic acetal or ketal structure of the ethers (VII) can now be cleaved by conventional acidic hydrolysis methods. The cyclic ketals, where $R^6$ and $R^7=CH_3$, are particularly susceptible to acidic cleavage. Typically, the ether (VII) is dissolved in methanol/water mixtures, and the pH is adjusted to about pH=1 by addition of hydrochloric acid. Short time heating or refluxing of the mixture results in nearly quantitative cleavage of the cyclic ketal group to produce the polymerizable hydroxy compounds (I) of this invention, which can be isolated, for example, by filtration and purified, for example, by crystallization techniques.

Representative examples of stabilizer hydroxy compounds of formula (I) include:

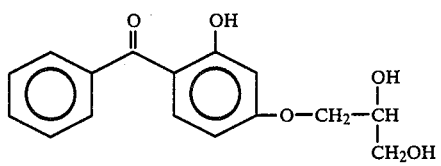
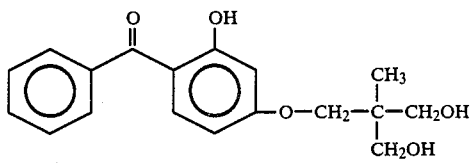
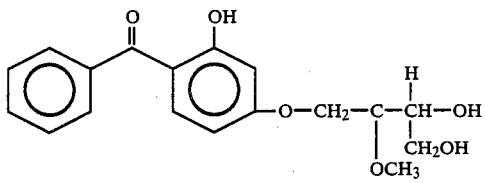
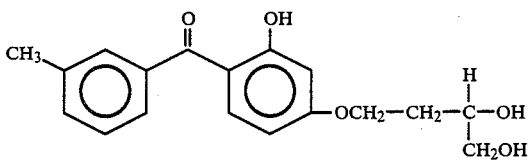
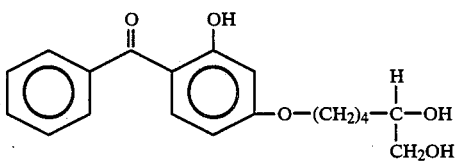
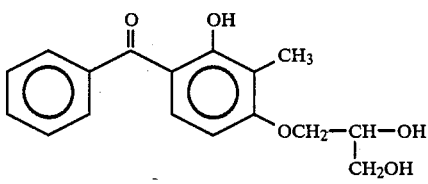
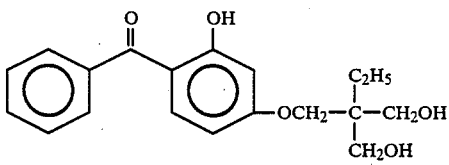
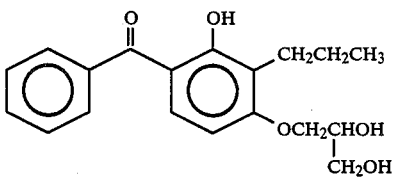
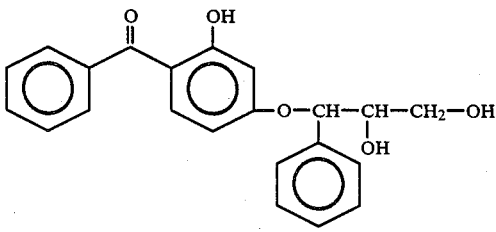

-continued
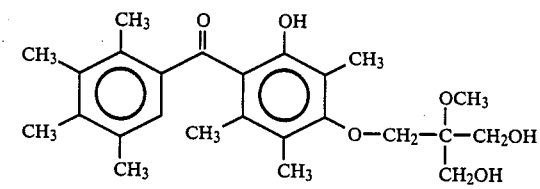
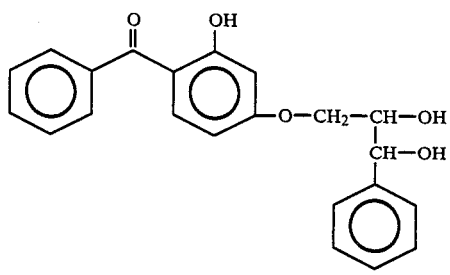
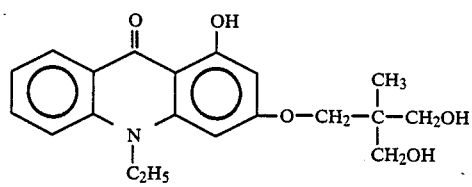
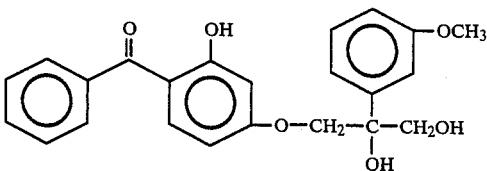
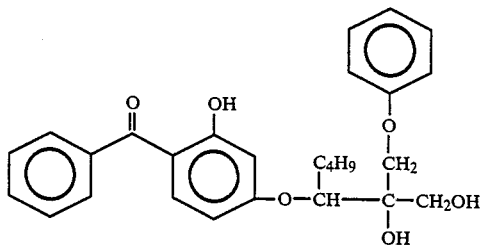
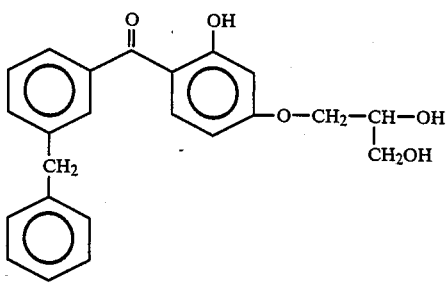
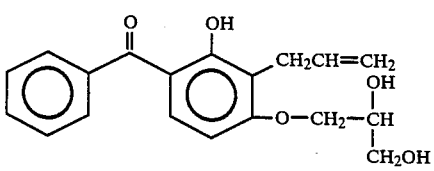

-continued
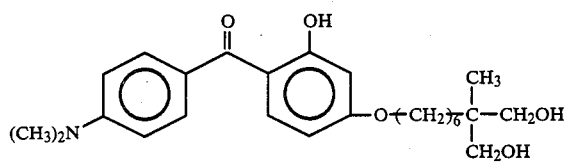
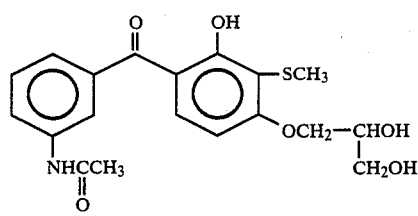
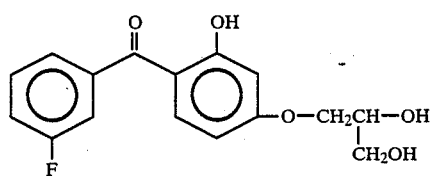
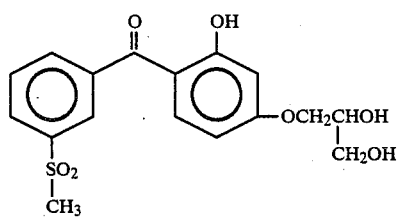
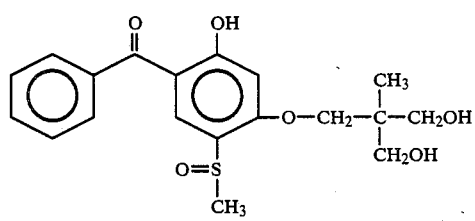
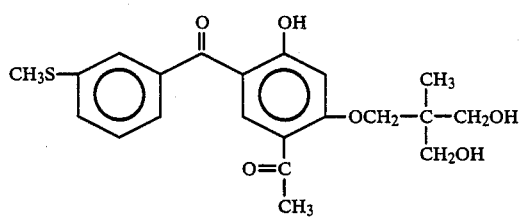
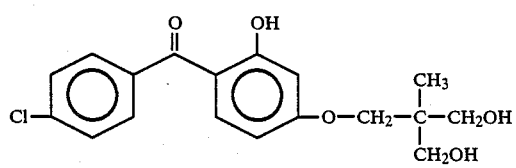

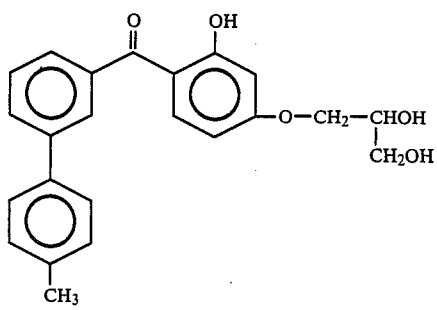
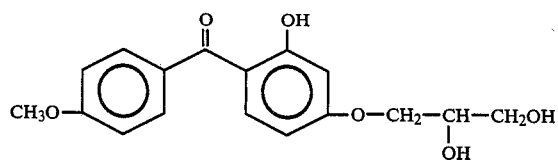
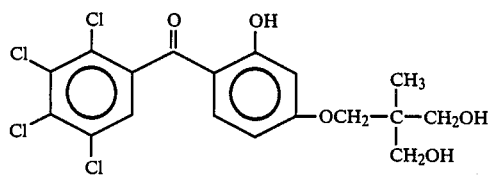
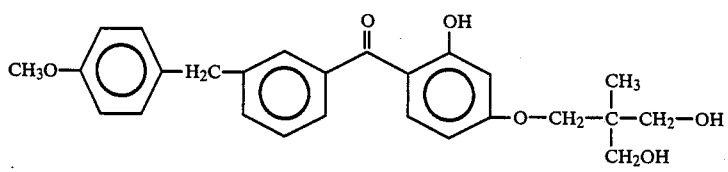
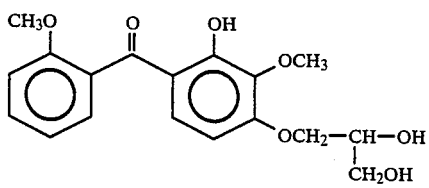
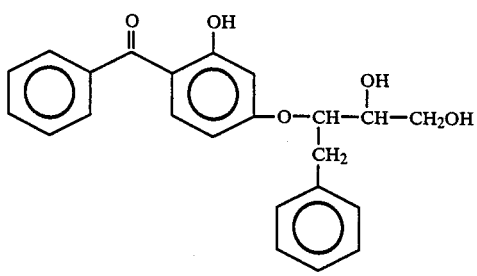
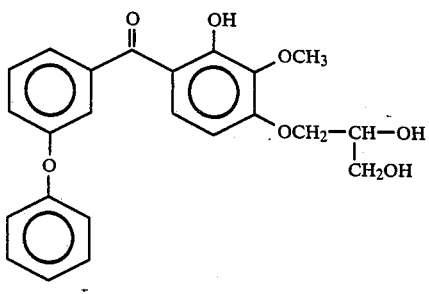

-continued
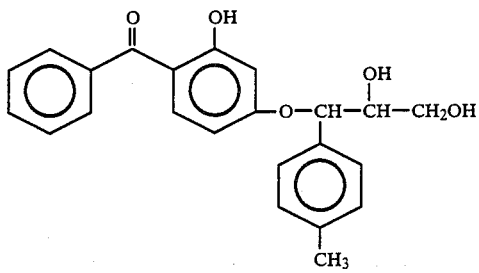
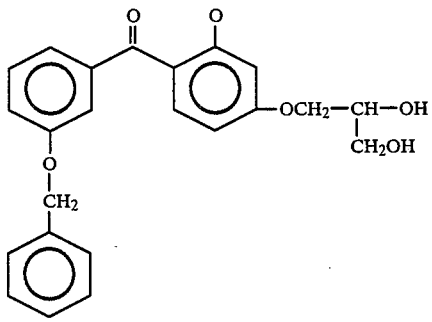
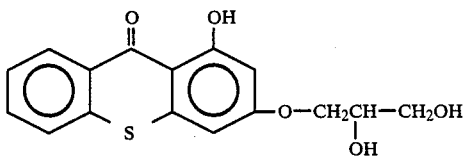
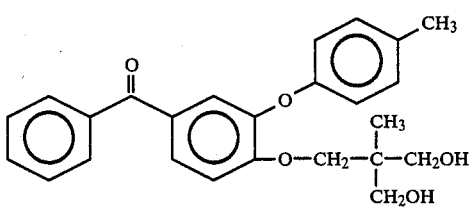
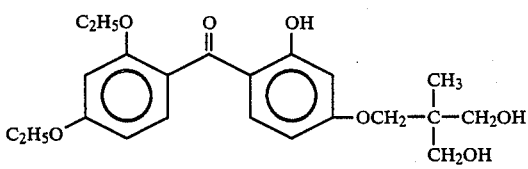
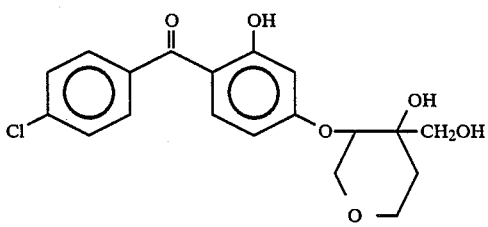
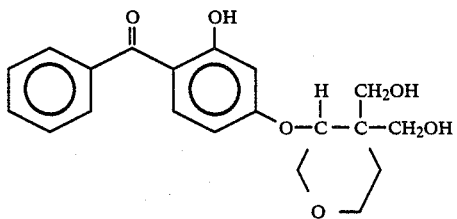

-continued
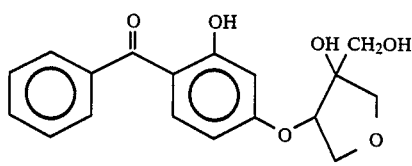
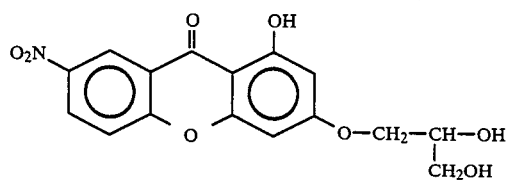
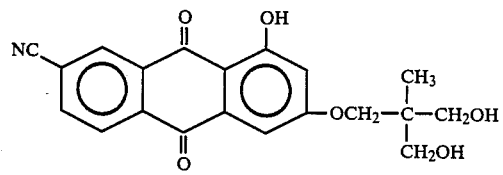
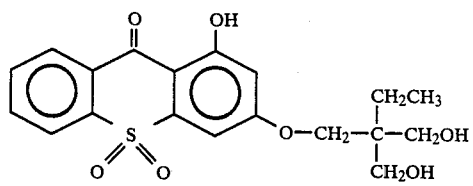
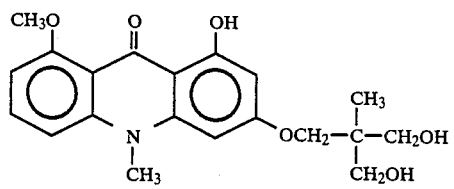
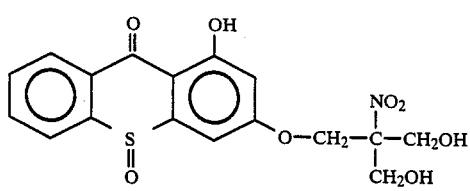
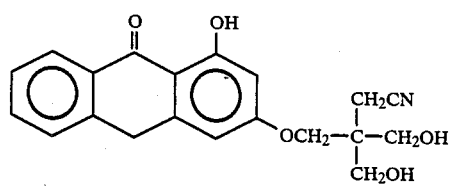
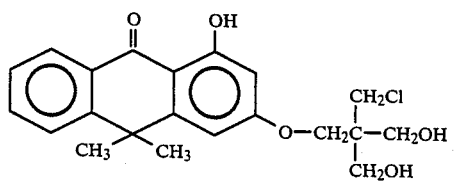

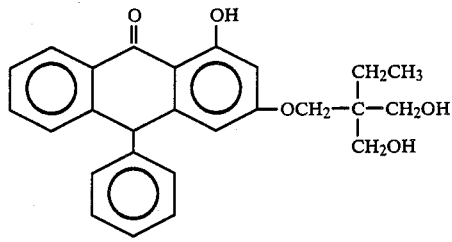

The hydroxy compounds of structure (I) can be incorporated into typical step growth polymers, e.g., polyesters, polycarbonates, polyurethanes, etc. or combinations thereof. Generally, the stabilizer hydroxy compound (I) is mixed with other diols and cocondensed with dicarboxylic acids such as phthalic acid, terephthalic acid, adipic acid, maleic acid, malonic acid, glutaric acid, oxalic acid, succinic acid, and malic acid, their esters, and their acid chlorides, phosgene, or bischloroformates such as 1,2-ethanedioldichloroformate, 1,4-butanedioldichloroformate, 1,6-hexanedioldichloroformate, 1,3-dichloroformyloxybenzene, 1,4-dichloroformyloxybenzene, bisphenol A-dichloroformate, etc., or diisocyanates, such as toluene diisocyanate, hexamethylene diisocyanate, and tetramethylene diisocyanate, etc., to produce the stabilizer-incorporated polymers. Synthetic techniques for preparing step growth polymers from hydroxy compounds are well known in the art and any of these standard methods may be used to prepare these polymers. See for example, the text G. Odian, "Principles of Polymerization", 2d Ed., John Wiley & Sons, NY (1981).

Representative examples of polymers within the present invention are as follows:

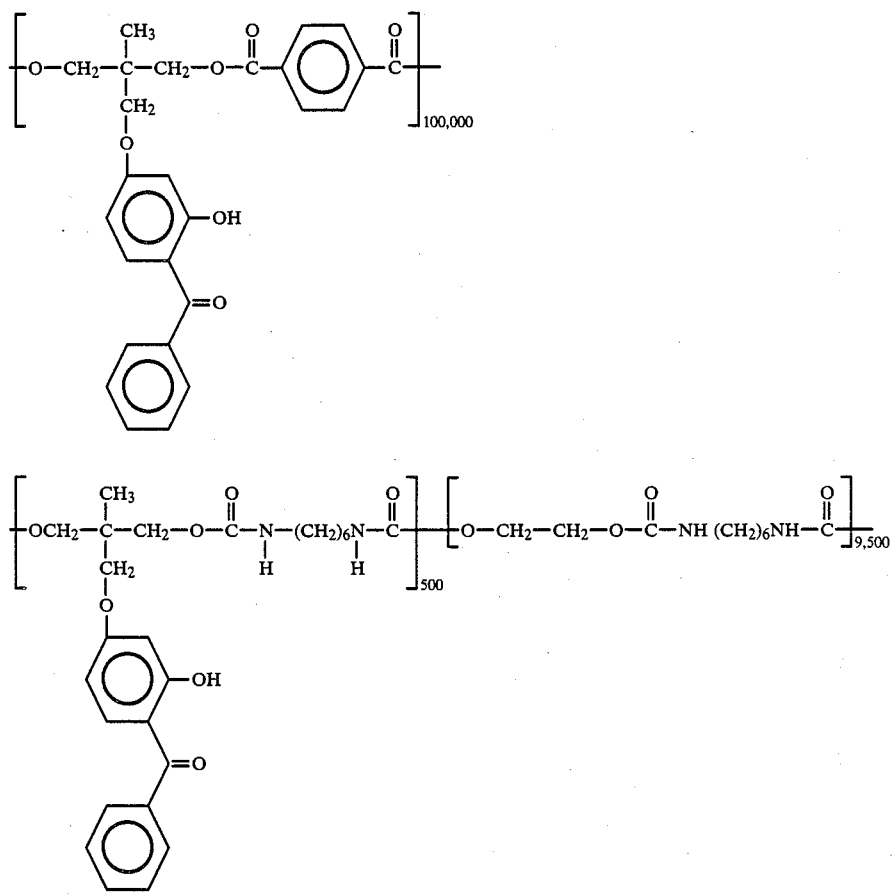

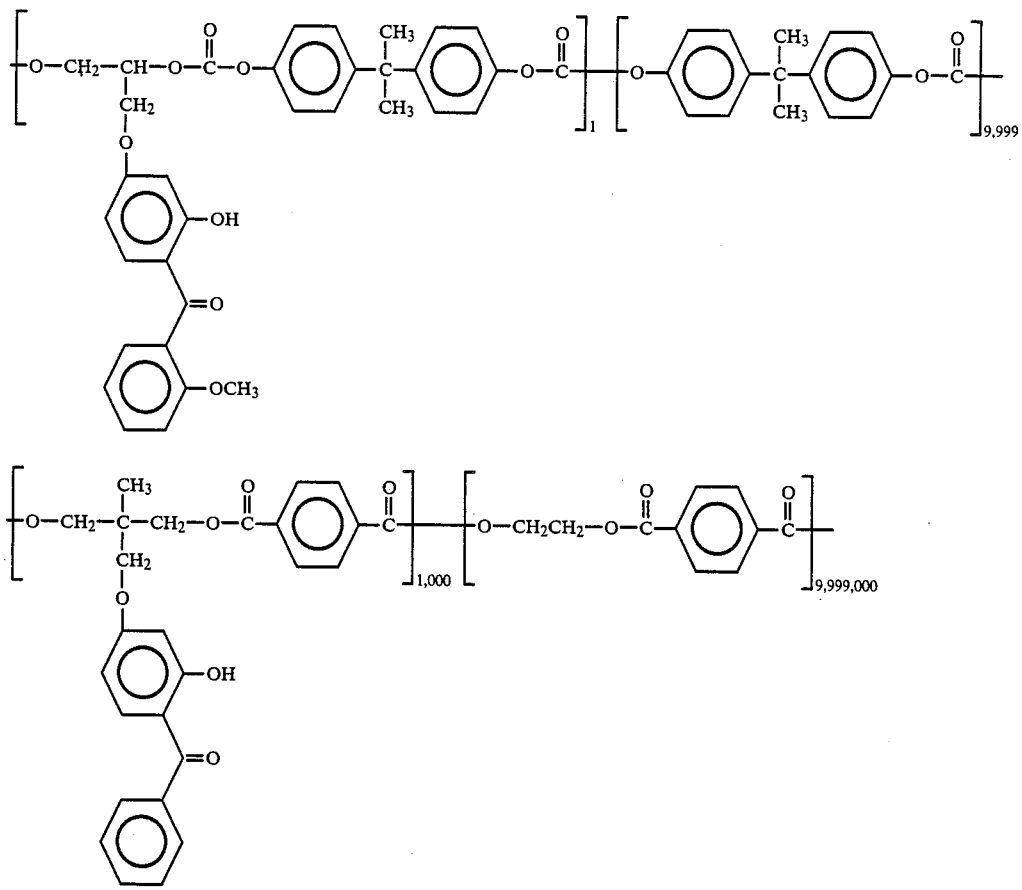

The examples below give some typical conditions for incorporating the stabilizers of the invention into polymers.

Polymers of the invention are useful as fibers as protective films, and as supports for other materials and are highly resistant to UV and sunlight degradation. Polymer films incorporating the polymeric UV stabilizers of the invention show good processability and, when compared in accelerated weathering tests with polymers without UV stabilizers, show superior color stability, mechanical performance and reduced leachable fractions that arise from degradation (e.g., weathering) reactions.

It is envisioned within the scope of the present invention to provide physical blends of the polymers of the invention with compatible monomers and/or polymers to provide UV stabilized materials.

Objects and advantages of this invention are further illustrated by the following examples, but the particular materials and amounts thereof recited in these examples, as well as other conditions and details, should not be construed to unduly limit this invention.

EXAMPLE 1

Synthesis of stabilizer hydroxy compound Ia

A mixture of 26.4 g of solketal (Aldrich Chemical Co., Milwaukee, WI) and 41.2 ml of triethylamine in 100 ml methylene chloride was treated dropwise with 22.8 g of methanesulfonyl chloride at 0° C. followed by stirring at 0° C. for 15 minutes. After quenching the reaction with ice water, the organic layer was separated, washed with 10% hydrochloric acid, saturated NaHCO$_3$ and saturated NaCl and the solvent was removed to give the solketal mesylate in 85% yield (boiling point, b.p., 110°–112° C. at 2 Torr).

A mixture of 42.8 g of 2,4-dihydroxybenzophenone and 8.0 g sodium hydride in DMF was treated with 63.0 g of solketal mesylate at 100° C. for 16 hours. The reaction mixture was poured into four-fold volume of ice cold water. The product separated as a solid and was filtered and recrystallized from methanol to give the solketal ether of 2,4-dihydroxybenzophenone in 85% yield.

A 25 g portion of the solketal ether of 2,4-dihydroxybenzophenone was dissolved in 300 ml of hot methanol and to it was added 50 ml of hot water. The pH was adjusted to 1 with HCl and the solution was refluxed for 90 mins. followed by stirring at room temperature for 18 hours. After evaporation of methanol, the aqueous solution was neutralized with sodium bicarbonate wherein the diol precipitated. It was filtered, washed with water and dried in vacuum over phosphorous pentoxide (P$_2$O$_5$). The yield of product from hydrolysis was quantitative and spectral analysis confirmed the structure for Ia, wherein R$^1$=H, R$^2$=H, m=0, x=1, y=0, A=B=H.

EXAMPLE 2

Synthesis of stabilizer hydroxy compound Ib

A mixture of 30 g of 1,1,1-tris(hydroxymethyl)ethane (Aldrich Chemical Co., Milwaukee, WI), 85 ml of acetone and 80 ml of petroleum ether (b.p. 30°–75° C.) was acidified with 1.0 g of p-toluenesulfonic acid monohydrate and this mixture was refluxed for 24 hours with removal of water by azeotropic distillation. This was followed by neutralization with 1 g of sodium acetate and complete drying with anhydrous sodium sulfate. The liquid was filtered and the solvents removed under reduced pressure. The residue was distilled under vacuum to give 5-hydroxymethyl-2,2,5-trimethyl-1,3-dioxane in 90% yield.

A solution of 16 g of the above alcohol and 15 g of triethylamine in 50 ml of methylene chloride was cooled to 5° C. and 11.5 g of methanesulfonyl chloride was added dropwise. The mixture was then stirred at this temperature for 15 mins. and quenched with 50 ml of water. The organic layer was separated, washed with 10% hydrochloric acid, saturated NaHCO$_3$ solution and then dried with anhydrous sodium sulfate (Na$_2$SO$_4$). The product was distilled under a vacuum to give of the corresponding mesylate in 65% yield (b.p., 110°–115° C. at 0.3 Torr).

A mixture of 32.1 g of 2,4-dihydroxybenzophenone and 7.2 g of sodium hydride in DMF was treated with 35.7 g of the above mesylate at 100° C. for 3 hours. The product precipitated from the reaction mixture; it was filtered, washed with water and dried to give compound VII in 67% yield, where $R^1=H$, $R^2=CH_3$, $R^6=R^7=CH_3$, $x=y=1$, $A=B=H$.

A 2.5 g portion of the above ether was dissolved in 30 ml of hot methanol and to it was added 4 ml of hot water. The pH was adjusted to 1 with HCl and the solution was refluxed for 3 hours followed by stirring at room temperature for 16 hours. The solution was concentrated under reduced pressure, made slightly alkaline with NaHCO$_3$ and then completely dried under reduced pressure. The residual solid was washed with water to remove inorganic salts, and dried to give a quantitative yield of the stabilizer hydroxy compound Ib where $A=B=H$, $R^1=H$, $R^2=CH_3$, $x=1$, $y=1$, and $m=0$.

EXAMPLE 3

Synthesis of polyester of formula II above, wherein
$R^1=R^2=H$, $A=B=H$, $x=1$, $y=0$, $m=0$,
$R=-CH_2CH_2-$ and $D=$

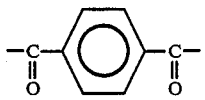

A mixture of 4.85 g dimethyl terephthalate, 1.42 g ethylene glycol, 0.12 g of 4(2,3-dihydroxypropoxy)-2-hydroxybenzophenone (Ia), 0.1 g of zinc acetate monohydrate and 2 mg of antimony trioxide was heated to a melt with removal of methanol. A vacuum was thereafter applied and the temperature brought to 205° C. to remove all volatiles. The product was recovered by precipitation from a hot dimethylsulfoxide (DMSO) suspension into methanol, filtration and drying. NMR and IR spectroscopies of polymer IIa indicated incorporation of the 2-hydroxybenzophenone moiety in the polyethylene terephthalate (PET). Extensive extraction of polymer IIa with methanol, which is a solvent for the stabilizer monomer, did not remove the stabilizer from the polymer as shown by IR and NMR spectroscopy moving the chemical binding of the stabilizer. Using various ratios of the stabilizer monomer to ethylene glycol, compositions of PET with as high as 26 mole% of the stabilizer groups were obtained.

EXAMPLE 4

Synthesis of polyurethane of formula II above, wherein
$R^1=H$, $R^2=CH_3$, $A=B=H$, $m=0$, $x=y=1$,

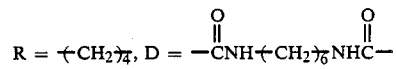

A mixture of 3.16 g of the diol (I) ($R^1=H$, $R^2=CH_3$, $A=B=H$, $x=y=1$) and 8.1 g of 1,4-butanediol was dissolved in 70 ml of dry DMF and 0.5 g of dibutyltin dilaurate (Alpha Products, Ventron, Denvers, MA) was added as a catalyst. The mixture was stirred under nitrogen and a solution of 17.6 of hexamethylene diisocyanate in 20 ml of DMF was slowly added. The solution became very viscous and soon a solid (IIb) separated. It was collected, continuously extracted with methanol, and allowed to dry. There was no loss of the stabilizer monomer from this polymer as shown by IR and NMR spectroscopies by the extensive extraction procedures described above.

EXAMPLE 5

Weathering of polymers

Polyethylene terephthalate films prepared from the polyester and stabilizer (Ia) (wherein $R^1=R^2=A=B=H$, $x=1$, $y=0$) incorporated in it, were weathered in a QUV accelerated weathering tester (Q-Panel Co., Cleveland, OH) for 100 hours. Polyethylene terephthalate reference films (Control, 3M St. Paul, MN) were also weathered under the same conditions. The samples were thereafter evaluated by the process of S. Krishnan et al. [S. Krishnan, S. B. Mitra, P. M. Russell, and G. Benz, ACS Division of Polymeric Materials Science and Engineering Preprints, 50, 470 (1984)] which showed that the stabilized polyethylene terephthalate was found to be significantly more resistant to photochemical degradation than were the unstabilized samples.

For example, after 100 hours of exposure in a QUV tester followed by aqueous extraction, the stabilizer-incorporated polymer showed 0.09 mg loss in weight per g of polymer, whereas the polymer without the stabilizer lost 0.17 mg per g of polymer; that is, almost twice as much material was extracted from the polymer without UV stabilization.

Various modifications and alterations of this invention will become apparent to those skilled in the art without departing from the scope and spirit of this invention, and it should be understood that this invention is not to be unduly limited to the following illustrative embodiments set forth herein.

We claim:
1. A polymer having the formula
wherein $R^1$ and $R^2$ are the same or different and each is selected from the group consisting of hydrogen alkoxyalkyl, aryl, aryloxyalkyl, alkoxyaryl, alkyl, aralkyl, and alkaryl groups, or $R^1$ and $R^2$ together can form an aliphatic cyclic structure of 5 to 7 atoms which include carbon and zero to two non-connected oxygen atoms, wherein $R^1$ and $R^2$ together total from zero to forty carbon atoms; x is an integer from 0 to 20, y is 0 or 1, provided that both x and y are not zero; m is 0 or 1; A and B are the same or different and represent zero to eight monovalent substitutents on the aromatic rings selected from the group consisting of (1) hydrogen, halogen, nitro, tertiary amino, amido, and cyano, and (2) alkyl, alkenyl, aryl, aralkyl, alkaryl, alkoxy, aryloxy, aralkyloxy, alkaryloxy, aryloxyalkyl, and thioalkyl, these groups having 1 to 20 carbon atoms and up to 6 non-connected oxygen and sulfur atoms; or A and B can be linked to said aromatic rings by a divalent keto, sulfoxide, and sulfone group, with the proviso that when m=0, W is not present, and then a benzophenone structure is present, and when m=1, then W is a single bond or a divalent group;

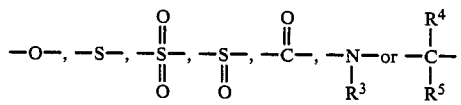

in which $R^3$ is an alkyl, alkoxyalkyl, aryl, aryloxyalkyl, alkoxyaryl, aralkyl, or alkaryl group; and $R^4$ and $R^5$ independently are the same as $R^1$ and $R^2$ which are defined above; R is any divalent organic group having 1 to 20 carbon atoms; D is

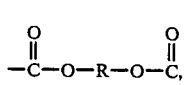

wherein R is as previously defined; P is at least one and q is zero or greater than zero, and when q is greater than zero the ratio of q to p is in the range of 1:10,000 to 10,000 to 1; and the number average molecular weight of the polymer is in the range of 1,000 to 10,000,000.

2. The polymer according to claim 1 wherein $R^1$, $R^2$, and $R^3$ are independently substituted by a non proton-donating moiety.

3. The polymer according to claim 2 wherein said non proton-donating moiety is halogen, or a nitro, cyano or an aldehyde group, or an acyl group having 1 to 10 carbon atoms, or aroyl group having 6 to 10 carbon atoms.

4. The polymer according to claim 1 wherein R is a linear or cyclic aliphatic or aromatic group, or combinations thereof, containing up to 3 non-connected N, S, and O hereto atoms.

5. The polymer according to claim 1 wherein R contains 1 to 10 carbon atoms and is an alkylene or arylene group, or an alkylene group interrupted by phenylene.

6. The polymer according to claim 1 blended with additional compatible monomers or polymers.

7. The polymer according to claim 1 comprising polyester units.

8. The polymer according to claim 1 comprising polyurethane units.

9. The polymer according to claim 1 comprising polycarbonate units.

10. A method for preparing a polymer comprising in sequence the steps:
(a) reacting, with an acid catalyst, a trihydroxy compound having the formula

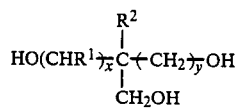

with an aldehyde or ketone

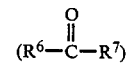

to provide a cyclic acetal or ketal having the formula

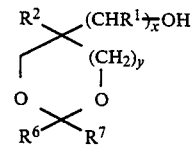

wherein
$R^1$ and $R^2$ are the same or different and each is selected from the group consisting of hydrogen, and alkyl, alkoxyalkyl, aryl, aryloxyalkyl, alkoxyaryl, aralkyl, and alkaryl groups, or $R^1$ and $R^2$ together can form an aliphatic cyclic structure of 5 to 7 atoms which include carbon and zero to two non-connected oxygen atoms, wherein $R^1$ and $R^2$ together total from zero to forty carbon atoms;
x is an integer from 0 to 20,
y is 0 or 1, provided that both x and y are not zero;
$R^6$ and $R^7$ are H, alkyl, aryl, or alkaryl, alkoxyalkyl, aryloxyalkyl, alkoxyaryl, or alkaryl groups, or $R^6$ and $R^7$ taken together can form an aliphatic cyclic structure having 5 to 7 carbon atoms and up to 2 non-connected oxygen atoms,
(b) reacting said resulting cyclic acetal or ketal with a leaving-group-containing compound to provide a leaving-group-containing cyclic acetal or ketal having the formula

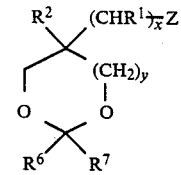

wherein $R^1$, $R^2$, x and y are as previously defined and z is a leaving group,
(c) reacting said resulting leaving-group containing cyclic acetal or ketal with a 2,4-dihydroxybenzophenone based compound to provide a 4-alkoxy-2-hydroxybenzophenone derivative of the formula

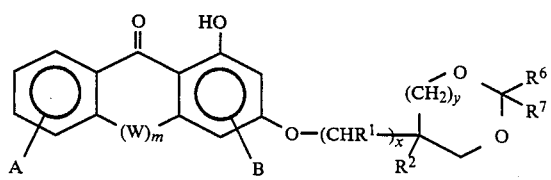

wherein m is 0 or 1, x and y are as previously defined, and W is a single bond or a divalent group

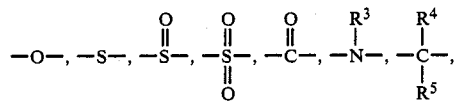

in which $R^3$ is an alkyl, alkoxyalkyl, aryl, aryloxyalkyl, alkoxyaryl, aralkyl, or alkaryl group; and $R^4$ and $R^5$ independently are the same as $R^1$ and $R^2$ which are as previously defined, and (d) subjecting said resultant 4-alkoxy-2-hydroxybenzophenone based compound to acid hydrolysis to provide said monomer having the formula

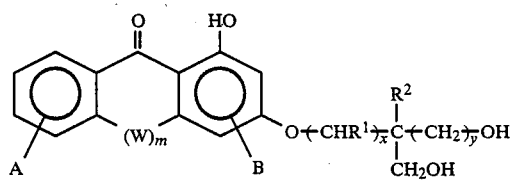

wherein $R^1$, $R^2$, A, B, W, x, y, and m are as previously defined, and (e) condensing said monomer with at least one multifunctional monomer containing acid, acid anhydride, acid chloride, ester, chloroformate, or isocyanate functionality, or with phosgene to provide a random polymer having the formula

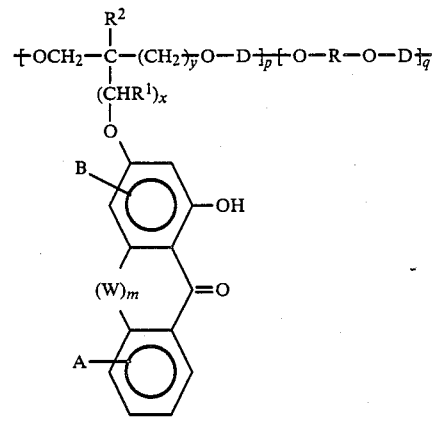

wherein
$R^1$, $R^2$, A, B, W, x, y, and m are as previously defined, and
R is any divalent organic group having 1 to 20 carbon atoms,
D is

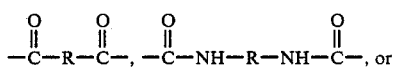 or

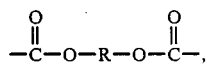

p is at least one,
q is zero or greater than zero, and when q is greater than zero, the ratio of q to p is in the range of 1:10,000 to 10,000 to 1, and said polymer has a number average molecular weight in the range of 1,000 to 10,000,000.

11. An article comprising the polymer according to claim 10.

12. The article according to claim 11 which is a fiber.

13. The article according to claim 11 which is a coating on a substrate.

14. The article according to claim 11 which is a support layer.

15. The polymer according to claim 5 wherein substituents A and B are substituted by at least one of halogen, nitro, tertiary amino, cyano, and amido groups.

16. The method according to claim 15 wherein groups $R^1$, $R^2$, and $R^3$ are independently substituted by a non proton-donating moiety.

17. The method according to claim 16 wherein said non proton-donating moiety is halogen, or a nitro, cyano or an aldehyde group, or an acyl group having 1 to 10 carbon atoms, or an aroyl group having 6 to 10 carbon atoms.

* * * * *

UNITED STATES PATENT AND TRADEMARK OFFICE
CERTIFICATE OF CORRECTION

PATENT NO. : 4,831,109

DATED : May 16, 1989

INVENTOR(S) : Mitra et al.

It is certified that error appears in the above-identified patent and that said Letters Patent is hereby corrected as shown below:

Col. 4, line 17, "b" should read -- be --.
Col. 27, line 67, "moving" should read -- proving --.
Col. 28, line 58, after "formula", insert -- 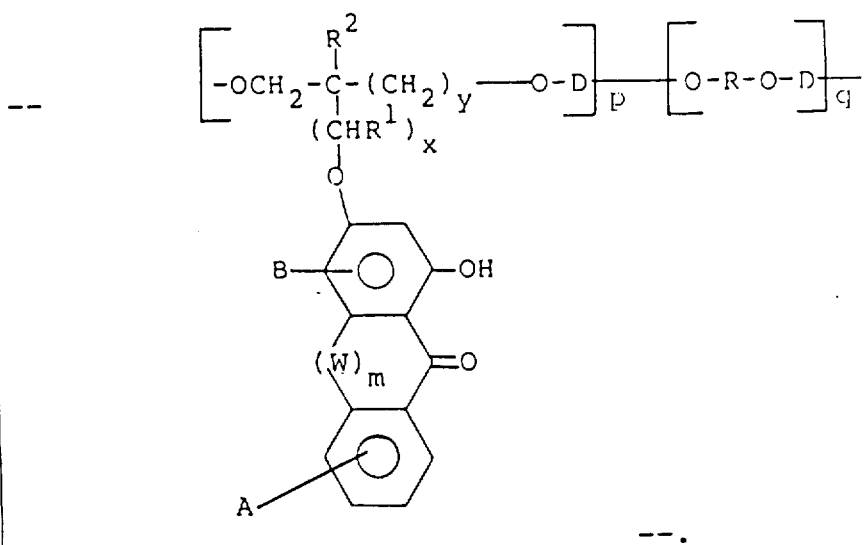 --.

UNITED STATES PATENT AND TRADEMARK OFFICE
CERTIFICATE OF CORRECTION

PATENT NO. : 4,831,109

DATED : May 16, 1989

INVENTOR(S) : Mitra et al.

It is certified that error appears in the above-identified patent and that said Letters Patent is hereby corrected as shown below:

Col. 28, line 60, after "hydrogen", insert -- , --.

Col. 29, line 34, "P" should read -- p --.

Signed and Sealed this

Twenty-second Day of December, 1992

Attest:

DOUGLAS B. COMER

*Attesting Officer*  *Acting Commissioner of Patents and Trademarks*